(12) United States Patent
Martinetti et al.

(10) Patent No.: US 8,673,017 B2
(45) Date of Patent: Mar. 18, 2014

(54) PROCESS FOR THE PREPARATION OF A BIOMIMETIC BONE SUBSTITUTE AND ITS USES

(75) Inventors: Roberta Martinetti, Forli' (IT); Daniele Pressato, Montegrotto Terme (IT); Laura Dolcini, Faenza (IT); Sergio Di Fede, Bologna (IT)

(73) Assignee: Fin-Ceramica Faenza S.p.A., Faenza (IT)

( * ) Notice: Subject to any disclaimer, the term of this patent is extended or adjusted under 35 U.S.C. 154(b) by 1086 days.

(21) Appl. No.: 11/995,908

(22) PCT Filed: Jul. 12, 2006

(86) PCT No.: PCT/IB2006/001925
§ 371 (c)(1),
(2), (4) Date: Apr. 22, 2008

(87) PCT Pub. No.: WO2007/010347
PCT Pub. Date: Jan. 25, 2007

(65) Prior Publication Data
US 2008/0199382 A1    Aug. 21, 2008

(30) Foreign Application Priority Data
Jul. 19, 2005  (IT) .............................. MI2005A1370

(51) Int. Cl.
*C01B 25/00*   (2006.01)

(52) U.S. Cl.
USPC ........ 623/23.56; 623/923; 423/308; 423/306; 424/602

(58) Field of Classification Search
USPC ............ 423/305–309, 311; 623/16.11, 23.56, 623/923; 106/462, 690; 427/2.27; 606/76, 606/77; 264/16, 19; 424/444; 523/115
See application file for complete search history.

(56) References Cited

U.S. PATENT DOCUMENTS

| | | | |
|---|---|---|---|
| 3,929,971 A * | 12/1975 | Roy | ............................. 423/308 |
| 4,481,175 A | 11/1984 | Iino et al. | |
| 6,024,985 A * | 2/2000 | Simkiss et al. | ................ 424/602 |
| 2002/0127260 A1 | 9/2002 | Riman et al. | |

(Continued)

FOREIGN PATENT DOCUMENTS

| | | |
|---|---|---|
| EP | 1 411 035 A2 | 4/2004 |
| JP | 11-29374 A | 5/1989 |
| JP | 10-216214 A | 8/1998 |
| KR | 2003 030 293 A | 4/2003 |
| WO | 03035576 A | 5/2003 |

OTHER PUBLICATIONS

Landi et al., "Nucleation of biomimetic apatite in synthetic body fluids: dense and porous scaffold development," 2005, Biomaterials, 26, pp. 2835-2845.*

(Continued)

*Primary Examiner* — Patricia L Hailey
*Assistant Examiner* — Colette Nguyen
(74) *Attorney, Agent, or Firm* — Pearne & Gordon LLP

(57) ABSTRACT

The object of the present invention is a process for obtaining a bone substitute of given chemical and physical characteristics and entirely similar to those of the mineral portion of natural bone tissue. The process substitutes Ca ions with Mg ions in a porous matrix; the process comprises a phase of contacting the matrix with a saline aqueous solution containing an effective quantity of Mg ions at a pressure greater than or equal to 1 bar.

16 Claims, 4 Drawing Sheets

(56) References Cited

U.S. PATENT DOCUMENTS

2003/0055512 A1* 3/2003 Genin et al. ............... 623/23.56
2004/0078087 A1* 4/2004 Kim et al. .................. 623/23.56
2005/0049715 A1 3/2005 Ito et al.
2005/0186249 A1 8/2005 Riman et al.

OTHER PUBLICATIONS

Preparation of Magnesium-Substituted Hydroxyapatite Powders by the Mechanochemical-Hydrothermal Method. By Whojciech L. Suchanek et al. Biomaterials 25 (2004) 4647-4657.*

Nucleation of Biomimetic Apatite in Synthetic Body Fluids: Dense and Porous Scaffold Development. By Elena Landi et al. Biomaterials 26 (2005) 2835-2845.*

Database WPI Week 200353, Derwent Publications Ltd., London, GB; AN 2003-565614, XP-002422837 & KR 2003 030 293 A (Inst Ceramic Technology) Apr. 18, 2003 Abstract.

Gibson, I. R. et al., "Preparation and characterization of magnesium/carbonate co-substituted hydroxyapatites", Journal of Materials Science, Materials in Medicine, Chapman and Hall, London, GB, vol. 13, No. 7, 2002, pp. 685-693, XP-002306881, ISSN: 0957-4530.

Suchanek, W. L. et al., "Preparation of magnesium-substituted hrdroxyapatite powders by the mechanochemical-hydrothermal method", Biomaterials, vol. 25, 2004, pp. 4647-4657, XP-002413209.

* cited by examiner

PROCESS FOR THE PREPARATION OF A BIOMIMETIC BONE SUBSTITUTE AND ITS USES

The object of the present invention is a process for obtaining a bone substitute of given chemical and physical characteristics, entirely similar to those of the mineral portion of a natural bone tissue.

The inorganic component of the human bone is primarily composed of calcium, phosphate ions ($Ca^{2+}$, $PO_4^{2-}$, that form the apatite phase), carbonate ions ($CO_3^{2-}$) and small percentages of other ions, such as $Mg^{2+}$ and $Na^+$, in particular.

The carbonate renders the bone-like tissue more "dynamic" (that is, stechiometrically unstable) and thus more easily reabsorbed by the osteoclasts.

The magnesium content favours in turn the kinetics of osteointegration, probably by a stimulating action on the increase of osteoblasts, and therefore on the secretion of proteins capable of generating a bone matrix.

One of the most widely used bone-like substitutes in today's surgery is represented by synthetic hydroxyapatite (HA) as such, whose formula will be indicated in the context of this invention as $Ca_{10}(PO_4)_6(OH)_2$.

However, this synthetic hydroxyapatite is not a perfect biomimetic substitute of natural bone tissue.

It does in fact not possess the same structural and conformational characteristics of the hydroxyapatite produced in situ by the organism for mineralization on collagen fibrils with a simultaneous, preferential partial carbonation of the same hydroxyapatite in position B.

As known, the position B in the hydroxyapatite structure corresponds to that occupied by the phosphate groups:

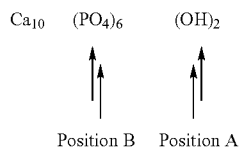

The carbonation in position B consequently involves the substitution to part of the phosphate groups by carbonate groups, thereby favouring the formation of a more biomimetic material with respect to the non-carbonated hydroxyapatite. However, even carbonated hydroxyapatite (for simplicity, referred to in the following as carbonate-hydroxyapatite or CHA) does not possess all the necessary characteristics to be a perfect biomimetic substitute of the mineral portion of natural bone tissue as its structure lacks, or eventually contains only in negligible, and at any rate inadequate necessary quantities of $Mg^{2+}$ ions.

Methods for preparing compounds capable of generating bone substitutes of various biomimetic degrees are known.

The U.S. Pat. No. 4,481,175, for instance, describes how to obtain a powdered hydoxyapatite composition, useful for generation of a bone substitute by wet, dry and/or sol gel chemical processes.

Hydroxyapatites and carbonate-hydroxyapatites can also be obtained from marine corals or from coelenterates having a $CaCO_3$-based skeleton, by treating them with appropriate acidic and/or saline solutions at a temperature well above the boiling point of water, and a pressure well above the atmospheric level.

In the course of said treatment, the above corals and coelenterates are brought into contact with solutions of $(NH_4)_2 HPO_4$ or of $(NH_4)_2HPO_4$ in $NH_4F$ (20 ppm); the solution pH is kept in a range of 8.5-9.0 (adjusting with $NH_4OH$, when necessary). The above described mixture is subjected to a pressure on average somewhere between 0.1 kbar and roughly 5 kbar, and a rather high temperature (up to 600° C.); the treatment time at the above conditions varies on the average from 24 to 48 hours, but may be prolonged up to about two weeks, depending on the temperature and pressure levels employed. After said treatment, the sample obtained is dried at about 80° C. for about 30 hours.

Other calcium phosphate-based structures may be realized by treating the calcareous skeleton of marine coelenterates with phosphate ion solutions ($PO_4^{2-}$).

For example, an anion exchange process run at the boiling temperature of the saline phosphate solution and at atmospheric pressure provides a mixed porous composite of calcite and hydroxyapatite.

The same process, run under high pressure and temperature conditions as described above, simply results in the formation of a porous hydroxyapatite.

However, none of the above mentioned processes allows obtaining a biomimetic material having characteristics analogous to those of the human bone structure.

There is therefore a need for making available a biomimetic bone substitute having a porosity analogous to that of human bone and also containing the necessary quantity of $Mg^{2+}$ ions.

One purpose of the present invention is to provide an adequate answer to the needs highlighted above.

This and further purposes, which will become evident from the detailed description to follow, have been achieved by the Applicant, who has unexpectedly found that it is possible to prepare a biomimetic human bone substitute by a process to substitute adequately $Ca^{2+}$ ions with $Mg^{2+}$ ions in a porous matrix based on hydroxyapatite (HA) or carbonate-hydroxyapatite (CHA) by treating said matrix with a saline aqueous solution containing an effective quantity of $Mg^{2+}$ ions.

In a preferred embodiment, said porous matrix is a solid, tridimensional, preformed porous scaffold.

One object of this invention is a process to substitute $Ca^{2+}$ ions with $Mg^{2+}$ ions in the above porous matrix, as outlined in the attached independent claim.

Another object of the present invention is the porous matrix obtainable by the above process, as outlined in the attached independent claim.

A further object of the present invention is the use of the porous matrix obtainable by the above process for the preparation of a biomimetic bone substitute, as outlined in the attached independent claim.

Preferred forms of embodiment of the present invention are outlined in the attached dependent claims.

The attached figures show the morphological characteristics of some of the preferred products realized by the process of the present invention.

Figure 1:
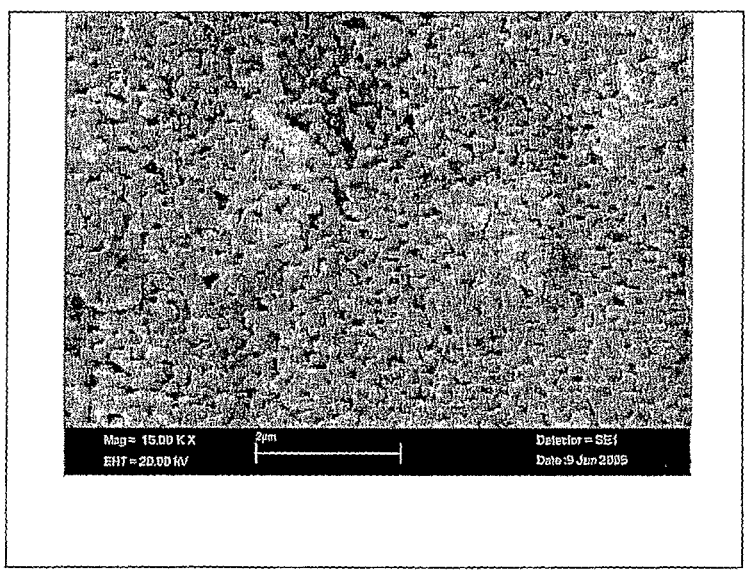
FIG. 1 shows the morphology, as revealed through an electronic scanning microscope (SEM), of the microstructure of a scaffold sample mainly of CHA, prior to being treated with a saline aqueous solution of $Mg^{2+}$— ions according to the process of the present invention.

The process according to the present invention is a process to substitute $Ca^{2+}$ ions with $Mg^{2+}$ ions in a porous matrix mainly of hydroxyapatite (HA) or carbonate-hydroxyapatite (CHA), comprising at least one phase of subjecting said matrix in contact with an aqueous saline solution containing an effective quantity of $Mg^{2+}$ ions at a pressure about equal to atmospheric pressure (variable with the altitude of one's location), or at a pressure ≥1 bar and a temperature of < or ≥100° C.

In a preferred embodiment, said porous matrix is a tridimensional solid scaffold.

In a particularly preferred embodiment, said porous scaffold is a preformed synthetic structure mainly of stechiometric hydroxyapatite (HA) or carbonate-hydroxyapatite (CHA) of a definite porosity and structure.

The total porosity of said matrix or of said scaffold is averagely in the range of 50% to 90% (by volume, with respect to the total matrix volume), and preferably of 75% to 85%.

The porosity range of said matrix or scaffold is on average from 0 to 500 micron (>95% by volume), for apatites of fine porosity; from 100 to 500 micron (>80% by volume) for apatites of medium porosity; and from 200 to 500 micron (>80% by volume) for apatites of large porosity.

In a particularly preferred embodiment, the porosity is similar to that of human bone, meaning on the average between 200 and 500 micron (total porosity of a spongy bone, from 60% to 90% by volume).

The quantity of carbonate present in said matrix or scaffold is preferably such as to approximate, as far as possible, that naturally present in human bone. For instance, the carbonate quantity is on average in the range from 0.1% to 12% by weight, with respect to the total scaffold weight, and preferably from about 2% to about 8% by weight.

For exemplifying and non limiting purposes, a particularly preferred form of embodiment for the purposes of the present invention are the porous scaffolds described in EP 1411035, particularly those obtained while following the preparation processes described in the examples form 1 to 5.

Preferably, the porous scaffold is treated with a saline aqueous solution containing $MgCl_2$ as a source of $Mg^{2+}$ ions.

In a particularly preferred embodiment, said saline solution is an aqueous $MgCl_2$ solution.

The $Mg^{2+}$ ion concentration in said solution is in the range of 0.1M to 4M; preferably from 0.2M to 3M; and more preferably from 0.5M to 2.5M.

In a particularly preferred embodiment said concentration is 2M.

The porous matrix or tridimensional scaffold and said saline aqueous $Mg^{2+}$ ion solution are present in a mutual weight ratio in the range of 1/3000 to 1/50;

preferably said ratio is about 1/1000, and more preferably about 1/500.

In a particularly preferred embodiment, said ratio is about 1/200.

The reaction of substituting the $Ca^{2+}$ ions with $Mg^{2+}$ ions is carried out at a pressure in the range of >1 bar to 5 bar; preferably, 1.5 bar to 3.5 bar: and more preferably 2 bar.

The temperature is in the range from >100° C. to 150° C.; preferably from 120° C. to 140° C.; and more preferably, from 130° C. to 138° C.

In a particularly preferred embodiment, the temperature is about 134° C.

Preferably, said at least one treating phase of said porous matrix or scaffold with said aqueous $Mg^{2+}$ ion solution is carried out in an autoclave for the time needed to obtain the desired degree of the $Mg^{2+}$ ion/$Ca^{2+}$ ion substitution. The duration of the treatment depends on the type of scaffold and on the operative conditions used; on average, a time in the range of 10 minutes to 80 minutes suffices; preferably, from 15 minutes to 60 minutes; and more preferably, from 20 minutes to 40 minutes.

In a preferred embodiment the time is about 20 minutes.

The conditions of the above substitution reaction are to be modulated so that the quantity of $Mg^{2+}$ ions to substitute the $Ca^+$ ions is, as far as possible, similar or superior to that present in the natural bone (0.47% by weight, with respect to the overall bone weight).

The final product obtained by the process of the invention is a porous matrix mainly of magnesium-hydroxyapatite or magnesium-carbonate-hydroxyapatite with a quantity of $Mg^{2+}$ ions in the range of 0.2% to 1.5% by weight with respect to the matrix weight; preferably, from 0.3% to 1.0% by weight; and more preferably, from 0.4% to 0.7% by weight.

In a particularly preferred embodiment, said final porous matrix is a solid, porous tridimensional scaffold mainly of magnesium-hydroxyapatite or magnesium-carbonate-hydroxyapatite with a quantity of $Mg^{2+}$ as described above.

Unexpectedly, the final product mainly of magnesium-hydroxyapatite or magnesium-carbonate-hydroxyapatite has shown to possess the same porosity characteristics as those of the corresponding source material, both in terms of total porosity and in terms of porosity distribution.

Even the micro and the macro-morphology of the porosity of the original synthetic scaffold are preserved, as evidenced in the attached figures.

The process, object of the present invention therefore advantageously allows obtaining a biomimetic bone substitute, of a totally synthetic nature, mainly of magnesium-hydroxyapatite (Mg-HA) or magnesium-carbonate-hydroxyapatite (Mg-CHA), wherein the micro and macro-morphologies of the porosity of the original synthetic scaffold are preserved.

A further object of the present invention is therefore also the solid porous tridimensional scaffold mainly of Mg-HA o.Mg-CHA, having the same $Mg^{2+}$ ion content and the same porosity of the original scaffold as obtained by the process of the present invention.

Said scaffold has proved to be particularly useful for preparing a biomimetic bone substitute.

In a particularly preferred embodiment, said bone substitute is characterized by a chemical composition highly comparable with that of the inorganic composition of the human bone, both in terms of degree of type B carbonation, as in terms of a partial substitution of the $Ca^{2+}$ ions with appropriate quantities of $Mg^{2+}$ ions and also of the porosity of the produced material.

Said bone substitute is thus distinguished by a particularly high degree of biomimicry.

In a preferred embodiment, the chemical formula of the bone substitute obtainable by the process of the present invention may be represented as follows:

$$Ca_{10(X+Z)}Na_xMg_z(PO_4)_{6-y}(CO_3)_y(OH)_2,$$

wherein:
x=0-0.6; preferably, 0.1-0.5; more preferably, 0.3;
y=0-2; preferably, 0.8-1.5; more preferably, 1;
z=0-1.5; preferably, 0.1-1; more preferably, 0.5;
and wherein the quantity of $Mg^{2+}$ (expressed as $Mg^{2+}$% by weight, with respect to the scaffold weight) is in the range from 0.2% to 1.5%; preferably from 0.3% to 1.0%; more preferably, from 0.4% to 0.7%.

In another preferred embodiment, the chemical formula of the bone substitute obtainable by the process of the present invention may be represented as follows:

$$Ca_{10-z}Mg_z(PO_4)_6(OH)_2,$$

wherein:
z=0-1.5; preferably, 0.1-1; more preferably, 0.5;
and wherein the quantity of $Mg^{2+}$ (expressed as $Mg^{2+}$% by weight, with respect to the scaffold weight) is in the range from 0.2% to 1.5%; preferably from 0.3% to 1.0%; more preferably, from 0.4% to 0.7%.

The process, object of the present invention, has shown to have a considerable number of advantages.

For example, it is possible to obtain bone substitutes with a biomimetic chemical composition with respect to the original human bone by starting from structures of a known porosity and a chemical composition of an entirely synthetic origin.

Moreover, it helps preserving the natural environment (it is no longer necessary to use coral structures).

A biomimetic bone substitute is obtained with a low expenditure of energy, as the process is carried out at low temperature and for a limited amount of time.

The degree of $Mg^{2+}/Ca^{2+}$ substitution in the preformed scaffold turns out to be more homogeneous with respect to that which would be obtained by preparing bone substitutes starting from Mg-HA or Mg-CHA powders.

In this case, the thermal processes said powders must be subjected to in order to induce their consolidation into a porous structure (with the use of temperatures in the range of 500° C. to 800° C.) cause the migration of the $Mg^{2+}$ ions from the interior of the structure to the surface, thus obtaining devices with a non-homogeneous magnesium content.

This negative effect is more marked especially when operating on porous structures based on CHA.

On the contrary, as shown before, the process, object of the present invention, does not modify the morphological characteristics of the porous support, meaning that the micro and macro-porosities of the original scaffold do not undergo variations.

The bone substitute obtainable by the process, object of the present invention, can be used for preparing devices capable of regenerating and repairing bone tissues in all fields of reconstructive and regenerative surgery (orthopaedics, dentistry, neurosurgery etc.).

Moreover, said product may be used as such or in association with materials of natural and/or synthetic origin such as for instance staminal cells, platelet concentrate, marrow concentrate, growth factors and other active ingredients capable of implementing its osteoconductive capabilities.

The product may also be used under various forms, such as small preformed blocs, tailor-made forms and chips, depending on the various application requirements.

The following experimental section illustrates, for merely exemplifying in a non-limitative manner, some of the preferred embodiments of the invention.

EXAMPLE 1

Partial substitution of the $Ca^{2+}$ ion with the $Mg^{2+}$ ion in a tridimensional porous scaffold mainly of carbonated hydroxyapatite.

3 samples of a synthetic bone substitute mainly of carbonate-hydroxyapatite in position B have been prepared by following the experimental procedure of Example 5 of the patent application EP 1 411 035 A2.

Said samples, characterized by a medium-large porosity of 83% by volume, are placed in a steel cup inside an autoclave, in which chamber a 2M $MgCl_2$ solution is poured.

The solution is prepared at the desired concentration by using the compound $MgCl_2.6H_2O$ (203.30 g/mole).

The weight ratio of porous sample to solution inside the autoclave is about 0.5/100.

Once the autoclave containing both the solution and the porous samples is ready, the process parameters are set up as follows:

pressure 2 bar and at a temperature of 134° C. for a treating time of 20 minutes.

The same experiment is repeated, under the same experimental conditions, on three other samples prepared as described above, by using a solution of 0.2M $MgCl_2$.

The quantity of calcium substituted by magnesium was verified in a comparative manner, by analyzing the samples untreated and treated by the process of the present invention. The data obtained were related to the chemical characteristics of a bone of human origin.

The following Tale 1 reports the data of the chemical characterization of the treated samples vs. the untreated samples obtained by a chemical analysis of the samples by ICP (inductively coupled plasma spectroscopy).

TABLE 1

| Sample | Mg/Ca (Wt. %) | (Ca + Mg)/P molar | Mg (Wt %) |
| --- | --- | --- | --- |
| Natural bone | — | 1.77 | 0.47 |
| Untreated CHA | 0.52 | — | 0.13 |
| Treated CHA (0.2M) | 2.80 | 1.85 | 0.62 |
| Treated CHA (2 M) | 4.20 | 1.91 | 0.91 |

Figure 2:
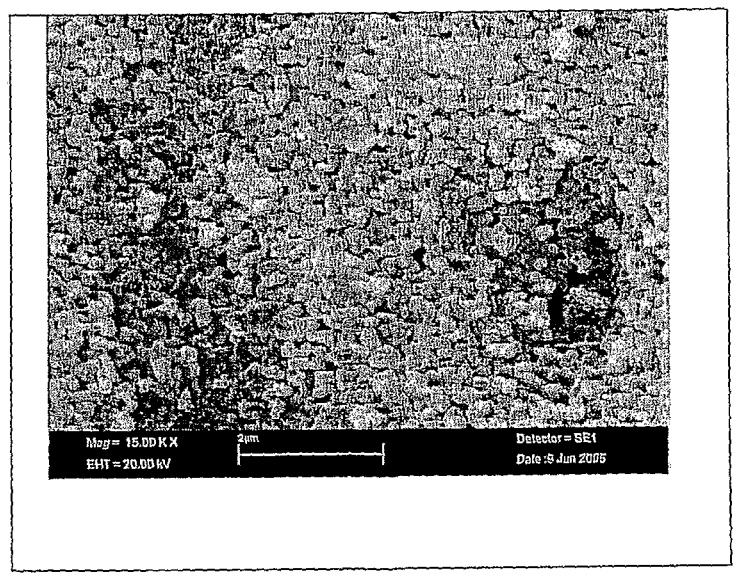
FIG. 2 shows the morphology, as revealed through an electronic scanning microscope (SEM), of the microstructure of a sample mainly of CHA scaffold treated with an aqueous $Mg^{2+}$ saline solution according to the process of the present invention.

The same samples were analyzed from a morphological viewpoint with an electronic scanning microscope (ESM), both before and after treatment with $MgCl_2$ (FIGS. 1 and 2), while other information on the chemical composition of the portions analyzed by the ESM were identified by an EDS (Energy Dispersion Spectroscopy) investigation.

The EDS investigation confirms that the treated samples have an Mg content, in % by weight, superior to that of the untreated samples (from 0.05 to 0.2% by weight in untreated samples; from 0.78 to 0.98% by weight for the samples treated with a 0.2 M $MgCl_2$ solution; and from 1.53 to 1.66% by weight for the samples treated with a 2M $MgCl_2$ solution.

In particular, it can be seen from the EDS investigation that the Mg-content is slightly higher at the surface vs. the fracture (0.98% and, respectively, 1.66%), or in the centre of the material (0.78% and, respectively, 1.53%). This slight difference in concentration is due to the fact that the $Mg^{2+}$ ion has a smaller size than the $Ca^{2+}$ ion, and therefore favours migrating to the surface of the materials and for this reason one finds a higher concentration in the surface than in the fracture.

Apart from this minimal disparity, the investigation confirms however, on the whole, that the introduction of $Mg^{2+}$ ions into the hydroxyapatite structure turns out to be substantially homogeneous throughout the sample analyzed.

EXAMPLE 2

Introduction of the $Mg^{2+}$ ion into the crystalline structure of a porous scaffold based on synthetic hydroxyapatite.

3 samples of a synthetic bone substitute mainly of hydroxyapatite have been prepared by following the experimental procedure of Example 4 of the patent application EP 1 411 035 A2.

Said samples, characterized by a medium porosity of about 80% by volume are placed in a steel cup inside an autoclave filled with a 2M $MgCl_2$ solution.

The solution is prepared at the desired concentration by using the compound $MgCl_2.6H_2O$ (203.30 g/mole).

The weight ratio of the porous sample to solution inside the autoclave is about 0.5/100.

Once the autoclave containing both the solution and the porous samples is ready, the process parameters are set up as follows:

pressure 2 bar and a temperature of 134° C. for a treating time of 20 minutes.

The quantity of magnesium substituted was verified in a comparative manner, by analyzing the samples untreated and treated by the process of the present invention.

The data obtained were related to the chemical characteristics of a bone of human origin.

The following Table 2 reports the data of the chemical characterization of the treated samples vs. the untreated samples obtained by a chemical analysis of the samples by ICP (inductively coupled plasma spectroscopy).

TABLE 2

| Sample | Mg/Ca (Wt. %) | (Ca + Mg)/P molar | Mg (Wt %) |
|---|---|---|---|
| Natural bone | — | 1.77 | 0.47 |
| Untreated HA | 0.91 | — | 0.24 |
| Treated HA (2 M) | 1.60 | 1.87 | 0.52 |

Figure 3:
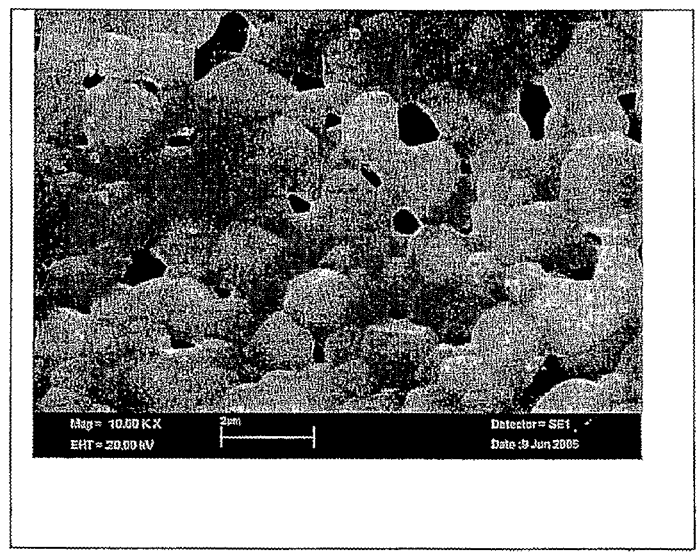
FIG. 3 shows the morphology, as revealed by an electronic scanning microscope (SEM), of the microstructure of a scaffold sample mainly of HA, prior to being treated with an aqueous $Mg^{2+}$ saline solution according to the process of the present invention.
Figure 4:
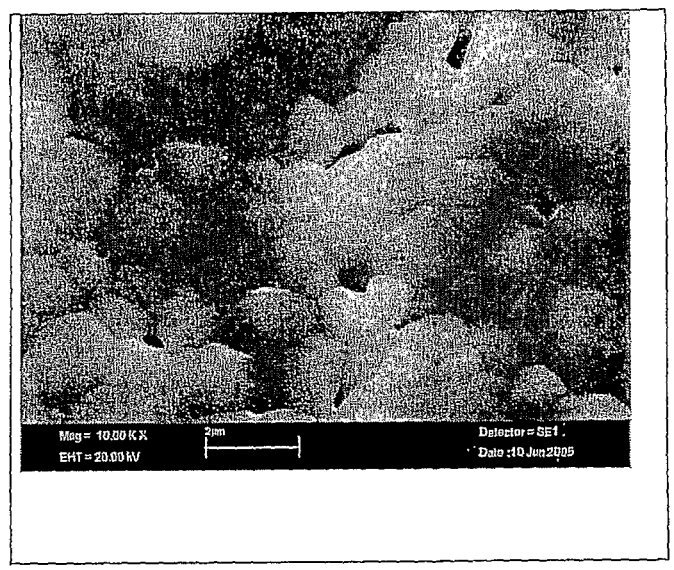
FIG. 4 shows the morphology, as reveled by an electronic scanning microscope (SEM), of the microstructure of a scaffold sample mainly of HA treated with an aqueous 0.2M $Mg^{2+}$ saline solution according to the process of the present invention.

The same samples were analyzed from a morphological viewpoint with an electronic scanning microscope (ESM), both before and after treatment with $MgCl_2$ (FIGS. 3 and 4), while other information on the chemical composition of the portions analyzed by the ESM were identified by an EDS (Energy Dispersion Spectroscopy) investigation.

The EDS investigation confirms that the treated samples have an Mg content, in % by weight, superior to that of the untreated samples (from 0.35 to 0.6% by weight for the untreated samples; from 0.42 to 0.46% by weight for the samples treated with a 0.2 M $MgCl_2$ solution; and up to 1.28% for those treated with a 2M $MgCl_2$ solution).

The invention claimed is:

1. A process for the preparation of a biomimetic bone substitute comprising:
   (a) providing a preformed solid three-dimensional porous scaffold comprising hydroxyapatite or carbonate-hydroxyapatite;
   (b) contacting extracorporeally said scaffold with a saline aqueous solution containing an effective concentration of $Mg^{2+}$ ions at a pressure greater than or equal to 1 bar, whereby during said contacting step $Ca^{2+}$ ions in the scaffold are substituted with $Mg^{2+}$ ions and the concentration of $Mg^{2+}$ ions in the scaffold is increased; and
   (c) obtaining a biomimetic bone substitute comprising magnesium-hydroxyapatite or magnesium-carbonate-hydroxyapatite having a content of $Mg^{2+}$ ions in the range of 0.2% to 1.5% by weight and a total porosity of 50% to 90% by volume, with respect to the total volume of the bone substitute, wherein both the total porosity and the porosity distribution of the bone substitute is the same as the total porosity and the porosity distribution of said three-dimensional porous scaffold.

2. The process according to claim 1, wherein said bone substitute has a total porosity of from 75% to 85% by volume.

3. The process according to claim 1, wherein said saline aqueous solution comprises said $Mg^{2+}$ ions at a concentration of from 0.1M to 4M.

4. The process according to claim 3, wherein said saline aqueous solution comprises said $Mg^{2+}$ ions at a concentration of from 0.2M to 3M.

5. The process according to claim 4, wherein said saline aqueous solution comprises said $Mg^{2+}$ ions at a concentration of from 0.5M to 2.5M.

6. The process according to claim 1, wherein said $Mg^{2+}$ ions are present as $MgCl_2$.

7. The process according to claim 1, wherein said porous scaffold and said saline aqueous solution are present in a weight ratio in the range from 1/3000 to 1/50.

8. The process according to claim 1, wherein the pressure is from 1 bar to 5 bar.

9. The process according to claim 1, wherein the pressure is from 1.5 bar to 3.5 bar.

10. The process according to claim 1, wherein said process is performed at a temperature ranging from 100° C. to 150° C.

11. The process according to claim 10, wherein the temperature is from 120° C. to 140° C.

12. The process according to claim 11, wherein the temperature is from 130° C. to 138° C.

13. The process according to claim 1, wherein step (b) is carried out in an autoclave over a time of from 10 minutes to 80 minutes.

14. The process according to claim 13, wherein step (b) is carried out in an autoclave over a time of from 15 minutes to 60 minutes.

15. The process according to claim 1, wherein the quantity of $Mg^{2+}$ ions is from 0.3% to 1.0% by weight with respect to that of the bone substitute.

16. The process according to claim 15, wherein the quantity of $Mg^{2+}$ ions is from 0.4% to 0.7% by weight with respect to that of the bone substitute.

* * * * *